(12) United States Patent
Martinez

(10) Patent No.: US 6,336,461 B1
(45) Date of Patent: Jan. 8, 2002

(54) TOOTH CLEANING DEVICE

(76) Inventor: Loren R. Martinez, 4911 W. Crocus, Glendale, AZ (US) 85306

( * ) Notice: Subject to any disclaimer, the term of this patent is extended or adjusted under 35 U.S.C. 154(b) by 0 days.

(21) Appl. No.: 09/765,468

(22) Filed: Jan. 22, 2001

(51) Int. Cl.[7] .......................... A45D 44/18; A45D 11/00; B08B 1/00; A61H 13/00
(52) U.S. Cl. .................... 132/309; 132/311; 15/104.94; 601/139
(58) Field of Search ................................ 132/309, 311; 15/227, 110, 167.1, 104.94; 206/368, 369, 63.5; 601/139

(56) References Cited

U.S. PATENT DOCUMENTS

| | | | | |
|---|---|---|---|---|
| 2,092,987 A | * | 9/1937 | Remington | 132/309 |
| 2,101,363 A | * | 12/1937 | De Rome | 132/309 |
| 2,686,325 A | * | 8/1954 | Silver | 15/104.94 |
| 2,966,691 A | * | 1/1961 | Cameron | 132/309 |
| 3,902,509 A | | 9/1975 | Tundermann et al. | |
| 3,934,299 A | * | 1/1976 | Regester | 15/104.94 |
| 4,292,705 A | * | 10/1981 | Stouffer | 15/110 |
| 4,335,731 A | * | 6/1982 | Bora | 132/309 |
| D313,317 S | | 1/1991 | Brunner et al. | |
| 5,228,433 A | | 7/1993 | Rosen | |
| 5,247,718 A | | 9/1993 | Victorian | |
| 5,487,201 A | * | 1/1996 | Hansen et al. | 15/104.94 |

* cited by examiner

*Primary Examiner*—Gene Mancene
*Assistant Examiner*—Robyn Kieu Doan

(57) ABSTRACT

A tooth cleaning device for cleaning teeth of plaque without using a toothbrush having bristles thereon. The tooth cleaning device includes a tubular member that is elongated and has a first end and a second end. The first end is open for accessing an interior of the tubular member. The second end is closed and has a generally convex shape. The tubular member comprises a cloth material. An elongated implement may be movably extended into the first end of the tubular member, such that the tubular member may be rubbed against the teeth of the user.

4 Claims, 3 Drawing Sheets

FIG. 5
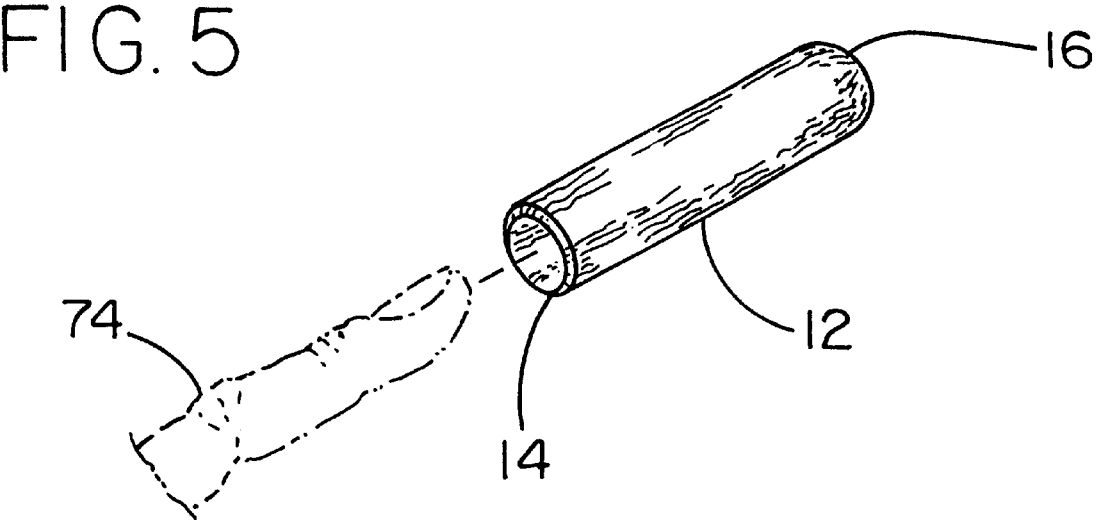
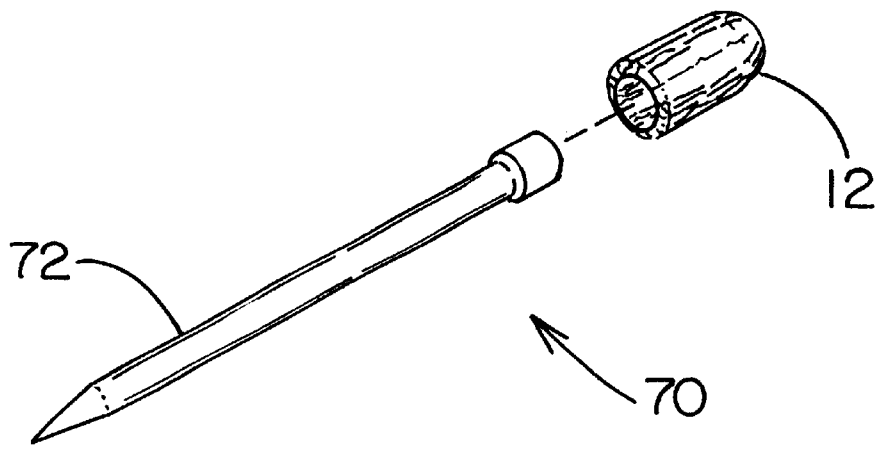
FIG. 6

TOOTH CLEANING DEVICE

BACKGROUND OF THE INVENTION

1. Field of the Invention

The present invention relates to tooth cleaning devices and more particularly pertains to a new tooth cleaning device for cleaning teeth of plaque without using a toothbrush having bristles thereon.

2. Description of the Prior Art

The use of tooth cleaning devices is known in the prior art. More specifically, tooth cleaning devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 3,902,509; U.S. Pat. No. 5,228,433; U.S. Pat. No. 3,934,299; U.S. Pat. No. 2,966,691; U.S. Pat. No. 5,274,718; and U.S. Des. Pat. No. 313,317.

While these devices fulfill their respective, particular objectives and requirements, the aforementioned patents do not disclose a new tooth cleaning device. The inventive device includes a tubular member that is elongated and has a first end and a second end. The first end is open for accessing an interior of the tubular member. The second end is closed and has a generally convex shape. The tubular member comprises a cloth material. An elongated implement may be movably extended into the first end of the tubular member, such that the tubular member may be rubbed against the teeth of the user.

In these respects, the tooth cleaning device according to the present invention substantially departs from the conventional concepts and designs of the prior art, and in so doing provides an apparatus primarily developed for the purpose of cleaning teeth of plaque without u sing a toothbrush having bristles thereon

SUMMARY OF THE INVENTION

In view of the foregoing disadvantages inherent in the known types of tooth cleaning devices now present in the prior art, the present invention provides a new tooth cleaning device construction wherein the same can be utilized for cleaning teeth of plaque without using a toothbrush having bristles thereon.

The general purpose of the present invention, which will be described subsequently in greater detail, is to provide a new tooth cleaning device apparatus and method which has many of the advantages of the tooth cleaning devices mentioned heretofore and many novel features that result in a new tooth cleaning device which is not anticipated, rendered obvious, Suggested, or even implied by any of the prior art tooth cleaning devices, either alone or in any combination thereof.

To attain this, the present invention generally comprises a tubular member that is elongated and has a first end and a second end. The first end is open for accessing an interior of the tubular member. The second end is closed and has a generally convex shape. The tubular member comprises a cloth material. An elongated implement may be movably extended into the first end of the tubular member, such that the tubular member may be rubbed against the teeth of the user.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new tooth cleaning device apparatus and method which has many of the advantages of the tooth cleaning devices mentioned heretofore and many novel features that result in a new tooth cleaning device which is not anticipated, rendered obvious, suggested, or even implied by any of the prior art tooth cleaning devices, either alone or in any combination thereof.

It is another object of the present invention to provide a new tooth cleaning device which may he easily and efficiently manufactured and marketed.

It is a further object of the present invention to provide a new tooth cleaning device which is of a durable and reliable construction .

An even further object of the present invention is to provide a new tooth cleaning device which is susceptible of a low cost of manufacture with regard to both materials and labor, and which accordingly is then susceptible of low prices of sale to the consuming public, thereby making such tooth cleaning device economically available to the buying public.

Still yet another object of the present invention is to provide a new tooth cleaning device which provides in the apparatuses and methods of the prior art some of the advantages thereof, while simultaneously overcoming some of the disadvantages normally associated therewith.

Still another object of the present invention is to provide a new tooth cleaning device for cleaning teeth of plaque without using a toothbrush having bristles thereon.

Yet another object of the present invention is to provide a new tooth cleaning device which includes a tubular member that is elongated and has a first end and a second end. The first end is open for accessing an interior of the tubular member. The second end is closed and has a generally convex shape. The tubular member comprises a cloth material. An elongated implement may be movably extended into the first end of the tubular member, such that the tubular member may be rubbed against the teeth of the user.

Still yet another object of the present invention is to provide a new tooth cleaning device that may be used in areas such as automobiles where water and toothpaste is inconvenient and not readily available.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 5 is a schematic perspective view of the present invention.

FIG. 6 is a schematic perspective view of the present invention.

DESCRIPTION OF THE PREFERRED EMBODIMENT

Figure 1:
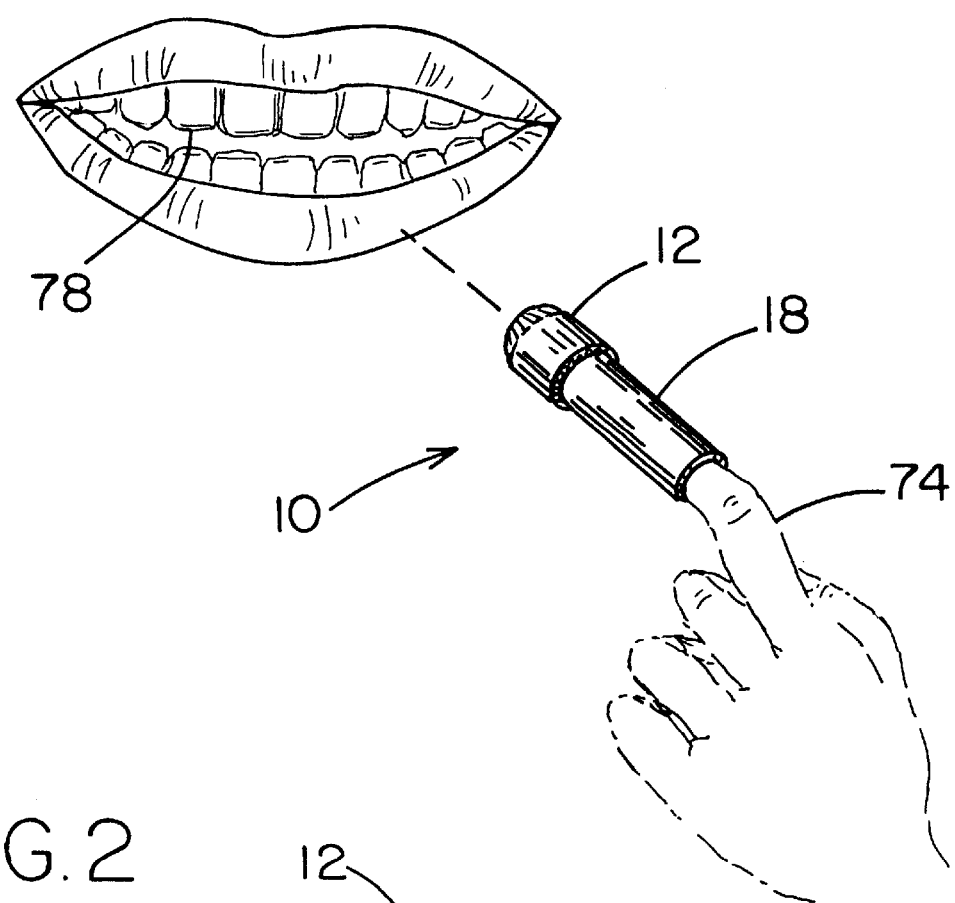
FIG. 1 is a schematic perspective view of a new tooth cleaning device according to the present invention.
Figure 2:
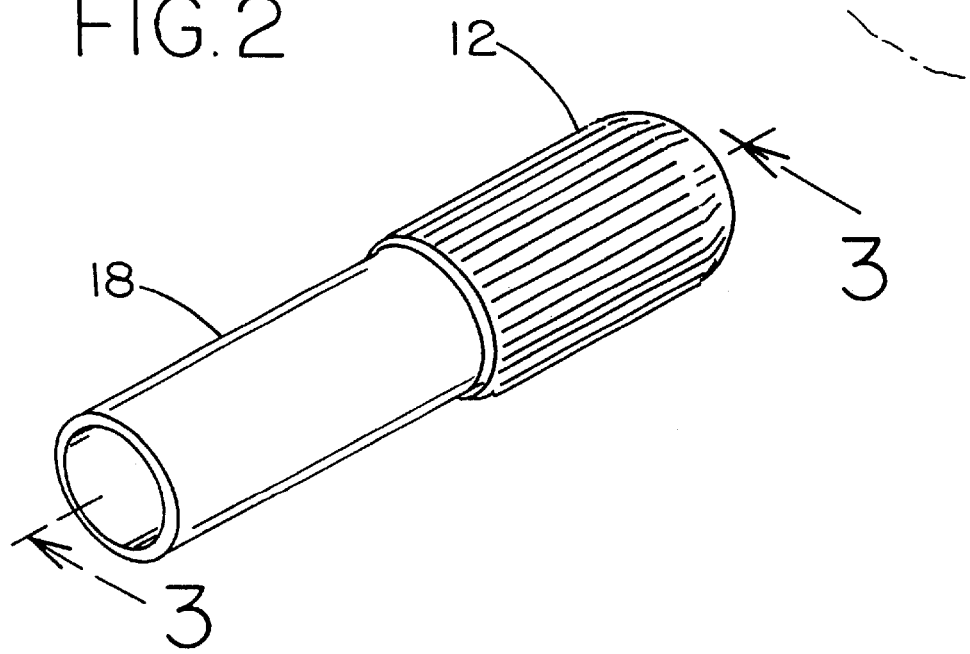
FIG. 2 is a schematic perspective view of the present invention.
Figure 3:
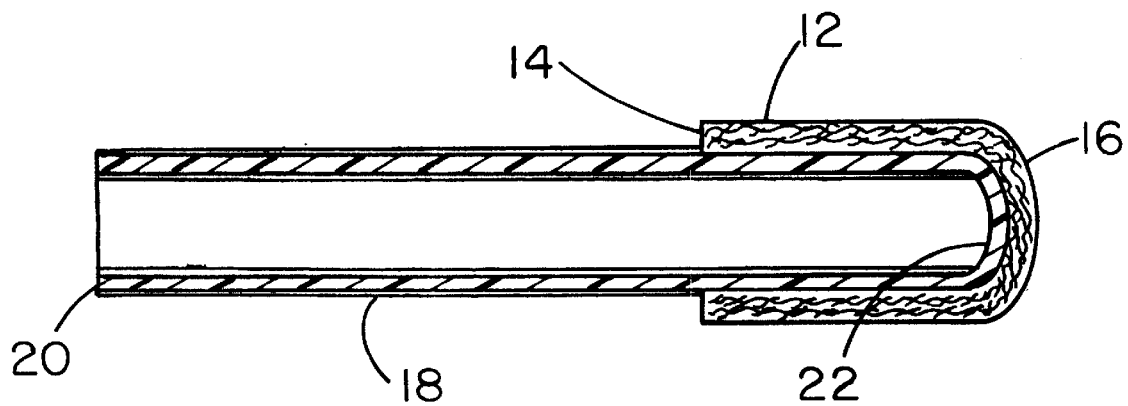
FIG. 3 is a schematic cross-sectional view taken along line 3—3 of the present invention.
Figure 4:
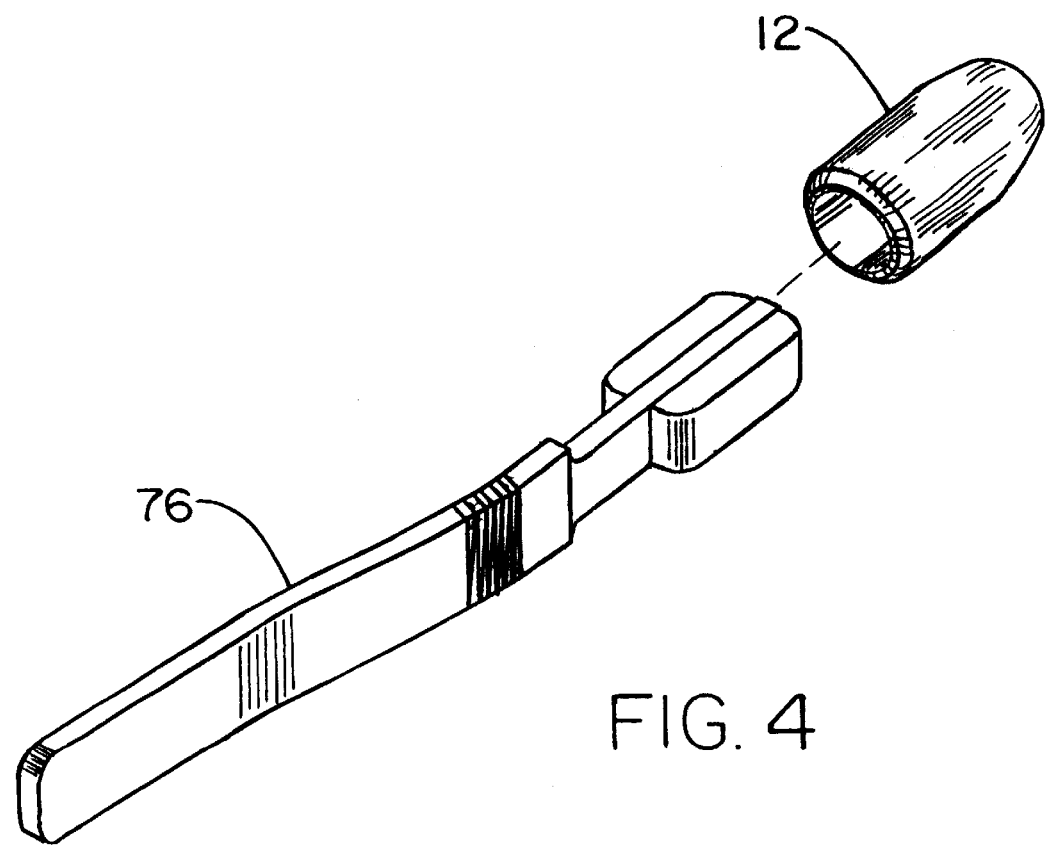
FIG. 4 is a schematic perspective view of the present invention.

With reference now to the drawings, and in particular to FIGS. 1 through 6 thereof, a new tooth cleaning device embodying the principles and concepts of the present invention and generally designated by the reference numeral 10 will be described.

As best illustrated in FIGS. 1 through 6, the tooth cleaning device 10 generally comprises the device is positionable over an elongated implement 70, such as a pencil 72, or finger 74 for rubbing against the teeth of a user. The device includes a tubular member 12, which is elongated and has a first end 14 and a second end 16. The first end 14 is open for accessing an interior of the tubular member 12. The second end 16 is closed and has a convex shape. The tubular member 12 has a length between the first and second ends generally between 1 inch and 12 inches and a width generally between ½ inch and 2 inches. The tubular member 12 comprising a cloth material which is preferably a cotton material.

A mounting member 18 comprises an elongated member having a first end 20 and a second end 22 The elongated member 18 is substantially hollow. The first end 20 of the mounting member 18 is open and the second end 22 is closed. The mounting member 18 has a length generally between 2 inches and 3 inches and width smaller than a width of the tubular member 12 such that the second end 22 of the mounting member is extendably movable into the first end 14 of the tubular member 12. The mounting member 18 comprises an elastomeric material.

In use, the elongated implement 70 is movably extendable into the first end 20 of the mounting member 18 either before or after the tubular member 12 is positioned on the mounting member 18. The tubular member 12 may be rubbed against the teeth 78 of the user. Also, the tubular member 12 may be positioned over the elongated implement 70 without the mounting member 18 and may have a length greater than 2 inches. Toothbrush handle-type implements 76 may be used so that the device 10 may be used in a manner similar to a conventional toothbrush. After use, the tubular member 12 may be thrown away. In this manner teeth may be cleaned in otherwise inconvenient areas Such as within the automobile or at work.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described and accordingly, all suitable modifications and equivalents may be resorted to, falling within the scope of the invention.

I claim:

1. A tooth cleaning device, said device being positionable over an elongated implement for rubbing against the teeth of a user, said device comprising:

a tubular member being elongated and having a first end and a second end, said first end being open for accessing an interior of said tubular member, said second end being closed and having a generally convex shape, said tubular member comprising a cloth material, wherein said elongated implement may be movably extended into said first end of said tubular member, wherein said tubular member may be rubbed against the teeth of the user;

a mounting member comprising an elongated member having a first end and a second end, said elongated member being substantially hollow, said first end being open and said second end being closed, said mounting member having a length greater than a length of said tubular member, said mounting member being removably extended into said first end of said tubular member, said mounting member comprising an elastomeric material, wherein said elongated implement is removably extendable into said first end of said mounting member such that said tubular member may be rubbed against the teeth of the user.

2. The tooth cleaning device as in claim 1, wherein said tubular member includes a plurality of tubular members.

3. The tooth cleaning device as in claim 1, wherein said tubular member has a length between said first and second ends generally between 1 inch and 2 inches, said tubular member having a width generally between ½ inch and 2 inches, said mounting member having a length generally between 2 inches and 3 inches and width smaller than a width of said tubular member.

4. A tooth cleaning device comprising:

a tubular member being elongated and having a first end and a second end, said first end being open for accessing an interior of said tubular member, said second end being closed and having a convex shape, said tubular member comprising a cloth material; and an elongated implement generally resembling a body of a toothbrush having a handle portion and a head portion;

a mounting member comprising an elongated member having a first end and a second end, said elongated member being substantially hollow, said first end being open and said second end being closed, said mounting member having a length generally between 2 inches and 3 inches and width smaller than a width of said tubular member such that said second end of said mounting member is extendably movable into said first end of said tubular member, said mounting member comprising an elastomeric material, wherein said elongated implement is movably extendable into said first end of said mounting member, wherein said tubular member may be rubbed against the teeth of the user.

* * * * *